US012614327B2

(12) United States Patent
Schmidt et al.

(10) Patent No.: US 12,614,327 B2
(45) Date of Patent: Apr. 28, 2026

(54) COMPUTER-IMPLEMENTED METHOD FOR HANDLING ARTIFACTS IN MULTI-ENERGY COMPUTED TOMOGRAPHY, X-RAY IMAGING DEVICE, COMPUTER PROGRAM AND ELECTRONICALLY READABLE STORAGE MEDIUM

(71) Applicant: Siemens Healthcare GmbH, Erlangen (DE)

(72) Inventors: Bernhard Schmidt, Furth (DE);
Katharine Grant, Rochester, MN (US);
Thomas Flohr, Uehlfeld (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 788 days.

(21) Appl. No.: 17/529,459

(22) Filed: Nov. 18, 2021

(65) Prior Publication Data

US 2022/0165003 A1 May 26, 2022

(30) Foreign Application Priority Data

Nov. 20, 2020 (EP) ..................................... 20209020

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/032* (2013.01); *A61B 6/5258* (2013.01);
(Continued)

(58) Field of Classification Search
CPC ................. G06T 11/008; G06T 7/0012; G06T 2207/10081; G06T 2207/10116;
(Continued)

(56) References Cited

U.S. PATENT DOCUMENTS

2010/0183214 A1  7/2010  McCollough et al.
2014/0133719 A1  5/2014  Wu et al.
(Continued)

FOREIGN PATENT DOCUMENTS

WO      WO 2016003957 A2      1/2016

OTHER PUBLICATIONS

Lin Yuan et al: "Development and validation of a segmentation-freevpolyenergetic algorithm for dynamic perfusion computed tomography"; Journal of Medical Imaging, Society of Photo-Optical Instrumentation Engineers ;1000 20th St. Bellingham WA 98225-6705 USA; vol. 3, No. 3; Jul. 1, 2016; p. 33503; XP060075333; ISSN: 2329-4302; DOI: 10.1117/1.JMI.3.3.03350.
(Continued)

*Primary Examiner* — Ping Y Hsieh
*Assistant Examiner* — Vaisali Rao Koppolu
(74) *Attorney, Agent, or Firm* — Harness, Dickey & Pierce, P.L.C.

(57) ABSTRACT

A computer-implemented method of an embodiment is for automatically estimating and/or correcting an error due to artifacts in a multi-energy computed tomography result dataset relating to at least one target material. In an embodiment, the method includes determining at least one first subregion of the imaging region, which is free from the target material and contains at least one, in particular exactly one, second material with known material-specific energy dependence of x-ray attenuation; for each first subregion, comparing the image values of the energy dataset for each voxel, taking into account the known energy dependence, to determine deviation values indicative of artifacts; and for at least a part of the at least one remaining second subregion of the imaging region, calculating estimated deviation values by interpolating and/or extrapolating from the determined
(Continued)

deviation values in the first subregion, the estimated deviation values being used as estimated error due to artifacts.

21 Claims, 4 Drawing Sheets

(51) Int. Cl.
*A61B 6/03* (2006.01)
*G06T 7/00* (2017.01)
*G06V 10/22* (2022.01)

(52) U.S. Cl.
CPC ............ *G06T 7/0012* (2013.01); *G06V 10/22* (2022.01); *G06T 2207/10081* (2013.01); *G06T 2207/10116* (2013.01); *G06T 2207/30061* (2013.01); *G06V 2201/03* (2022.01)

(58) Field of Classification Search
CPC ..... G06T 2207/30061; G06T 2211/408; G06T 11/005; A61B 6/032; A61B 6/5258; G06V 10/22; G06V 2201/03
See application file for complete search history.

(56) References Cited

U.S. PATENT DOCUMENTS

| | | | |
|---|---|---|---|
| 2015/0078507 A1 | 3/2015 | Kyriakou | |
| 2016/0123904 A1* | 5/2016 | Masood | G06V 10/761 |
| | | | 382/131 |
| 2016/0324499 A1* | 11/2016 | Sen Sharma | A61B 6/5258 |
| 2017/0186195 A1* | 6/2017 | Lin | A61B 6/482 |
| 2018/0293763 A1* | 10/2018 | Keeler | G06T 11/005 |
| 2019/0073804 A1* | 3/2019 | Allmendinger | G06N 20/00 |
| 2019/0380670 A1* | 12/2019 | Hofmann | |
| 2021/0012463 A1* | 1/2021 | Ramani | G06T 5/60 |

OTHER PUBLICATIONS

European Search Report for European Application No. 20209020.5 dated Feb. 8, 2021.

* cited by examiner

COMPUTER-IMPLEMENTED METHOD FOR HANDLING ARTIFACTS IN MULTI-ENERGY COMPUTED TOMOGRAPHY, X-RAY IMAGING DEVICE, COMPUTER PROGRAM AND ELECTRONICALLY READABLE STORAGE MEDIUM

PRIORITY STATEMENT

The present application hereby claims priority under 35 U.S.C. § 119 to European patent application numbers EP20209020 filed Nov. 20, 2020, the entire contents of which are hereby incorporated herein by reference.

FIELD

Example embodiments of the invention generally relate to a computer-implemented method for automatically estimating and/or correcting an error due to artifacts in a multi-energy computed tomography result dataset relating to at least one target material, wherein at least two three-dimensional energy datasets of an imaging region of a patient are acquired using an x-ray imaging device, in particular a computed tomography device, using different x-ray energy spectra, and the result dataset is determined by evaluating the energy datasets using material-specific energy dependencies of x-ray attenuation. Example embodiments of the invention further concerns an x-ray imaging device, a computer program, and an electronically readable storage medium.

BACKGROUND

Multi-energy computed tomography (multi-energy CT), sometimes also termed "spectral imaging" or "spectral CT", is a technique for energy-resolved x-ray imaging, in particular in medicine. This imaging technique exploits different energy dependencies of x-ray attenuation, for example to provide quantitative image data and/or reduce image artifacts by so-called material decomposition. Dual-energy CT, that is, imaging at two energy levels, is one of the most widely used variants of this technique. However, since the advent of photon-counting x-ray detectors, the potential for, in particular simultaneous, measurement at a larger number of energy spectra has been provided.

In particular, multi-energy imaging data, which may also be termed "spectral data", allows for the calculation of material-specific images, often called material maps, by, for example, applying a material decomposition algorithm to acquired energy datasets, each associated with a different energy spectrum and thus a different energy level. In the case of tumor/lesion characterization, tumor response assessment and/or other concrete tasks in medicine, the ability to extract iodine images/iodine maps from multi-energy data, and/or to quantify the iodine distribution in tissue as a result dataset, opens up a huge potential.

In known approaches, energy datasets are acquired at different x-ray energy spectra, that is, different energy levels. The energy datasets are then evaluated to determine a result dataset, for example a material map and/or other, in particular quantitative, values. In this evaluation, known material-specific energy dependences of x-ray attenuation for this material, are used. For example, the x-ray attenuation of two materials, for example iodine and calcium, may not only be different in an energy spectrum centered at 140 kV and an energy spectrum centered at 80 kV, but each material may also have its own characteristic changing pattern from 80 kV to 140 kV. Thus, the change in measured attenuation values between 80 and 140 kV (and/or other energy spectra) will enable differentiating such two materials, for example iodine and calcium.

However, for a reliable diagnosis, a reading physician has to be able to trust the quantitative information provided in the result dataset. On the other hand, similar to single-energy computed tomography images, the primary spectral computed tomography image data, that is, the energy datasets, can contain image artifacts caused by, for example, the acquisition technique, patient size, and/or patient motion. Within the material decomposition process or other evaluation processes, the errors induced by such artifacts are amplified and propagated, such that incorrect image values, in particular HU or density values, may be determined for the result dataset. Today, for the reading physician and/or, in general, user, it is not possible to recognize if image values of the result data set are correct or impacted by artifacts. If a user has doubts regarding the evaluation results, they will ask for an additional scan and/or a different imaging modality.

SUMMARY

At least one embodiment of the present invention provides information regarding image artifacts in result datasets and/or to provide result datasets with improved quality regarding artifacts.

Embodiments of the present invention are directed to a computer-implemented method, an x-ray imaging device, a computer program and an electronically readable storage medium. Advantageous embodiments are described in the claims.

At least one embodiment is directed to a computer-implemented method for automatically estimating and/or correcting an error due to image artifacts in a multi-energy computed tomography result dataset relating to at least one target material, wherein at least two three-dimensional energy datasets of an imaging region of a patient are acquired using an x-ray imaging device, in particular a computed tomography device, using different x-ray energy spectra and the result dataset is determined by evaluating the energy datasets using material-specific energy dependences of x-ray attenuation, according to the invention, the following steps are performed for estimation of the error due to artifacts:

determining at least one first subregion of the imaging region, which is free from the target material and contains at least one, in particular exactly one, second material with known material-specific energy dependence of x-ray attenuation, for each first subregion, comparing the image values of the energy dataset for each voxel, taking into account the known energy dependence, to determine deviation values indicative of artifacts, for at least a part of the at least one remaining second subregion of the imaging region, calculating estimated deviation values by interpolating and/or extrapolating from the determined deviation values in the at least one first subregion, wherein the estimated deviation values are used as estimated error due to artifacts.

At least one embodiment of the invention further concerns an x-ray imaging device, in particular a computed tomography device, comprising at least one acquisition arrangement, which comprises an x-ray source and an x-ray detector, and a control device configured to perform a method according to at least one embodiment of the invention. All features and remarks regarding the inventive method analogously apply to the x-ray imaging device according to at least one embodiment of the invention, such that the same advantages are achieved. In this manner, additional information and/or correction may be provided directly at the x-ray imaging device.

A computer program according to at least one embodiment of the invention can be, for example, loaded directly into a storage device of a control device of an x-ray imaging device and comprises program code/segments to perform the steps of a method according to at least one embodiment of the invention when the computer program is executed in the control device of the x-ray imaging device.

The computer program according to at least one embodiment of the invention may be stored on an electronically readable storage medium according to at least one embodiment of the invention, which thus comprises electronically readable control information stored thereon, wherein the control information comprises at least one computer program according to at least one embodiment of the invention and is configured such that a method according to at least one embodiment of the invention is performed if the electronically readable storage medium is used in a control device of an x-ray imaging device.

A computer-implemented method according to at least one embodiment of the invention for at least one of automatically estimating and automatically correcting an error due to artifacts in a multi-energy computed tomography result dataset relating to at least one target material, at least two three-dimensional energy datasets of an imaging region of a patient being acquired using an x-ray imaging device using different x-ray energy spectra, and a result dataset being determined by evaluating the energy datasets using material-specific energy dependences of x-ray attenuation, the computer-implemented method comprising:

determining at least one first subregion, of the imaging region, free from the at least one target material and containing at least one second material with known material-specific energy dependence of x-ray attenuation;

comparing, for each respective first subregion of the at least one first subregion, image values of the energy dataset for each voxel, taking into account the known energy dependence, to determine deviation values indicative of artifacts; and calculating, for at least a part of at least one remaining second subregion of the imaging region, estimated deviation values by at least one of interpolating and extrapolating from the determined deviation values in a respective first subregion, wherein the estimated deviation values are used as estimated error due to artifacts.

An X-ray imaging device according to at least one embodiment of the invention, comprising:

at least one acquisition arrangement including an x-ray source and an x-ray detector; and a controller to perform at least:

determining at least one first subregion, of the imaging region, free from the at least one target material and containing at least one second material with known material-specific energy dependence of x-ray attenuation;

comparing, for each respective first subregion of the at least one first subregion, image values of the energy dataset for each voxel, taking into account the known energy dependence, to determine deviation values indicative of artifacts; and calculating, for at least a part of at least one remaining second subregion of the imaging region, estimated deviation values by at least one of interpolating and extrapolating from the determined deviation values in a respective first subregion, wherein the estimated deviation values are used as estimated error due to artifacts.

A non-transitory computer program product according to at least one embodiment of the invention, storing a computer program which, when the computer program is executed on a control device of an x-ray imaging device, performs the method of an embodiment.

A non-transitory electronically readable storage medium, according to at least one embodiment of the invention, storing a computer program which, when the computer program is executed on a control device of an x-ray imaging device, performs the method of an embodiment.

BRIEF DESCRIPTION OF THE DRAWINGS

Other objects and features of the present invention will become apparent from the following detailed description of embodiments considered in conjunction with the accompanying drawings. The drawings, however, are only principle sketches designed solely for the purpose of illustration and do not limit the invention. The drawings show.

DETAILED DESCRIPTION OF THE EXAMPLE EMBODIMENTS

Figure 1:
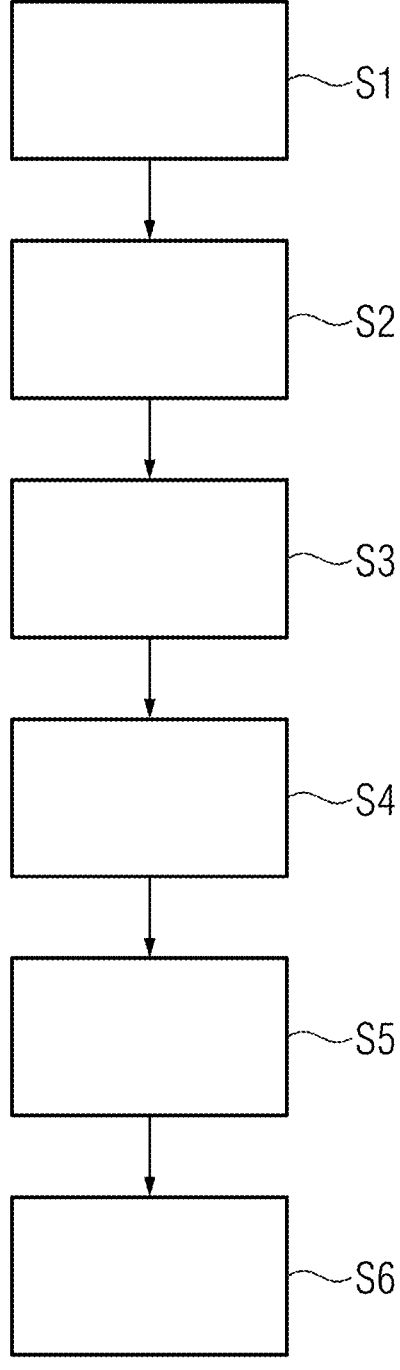
FIG. 1 a flow chart of an embodiment of a method according to an embodiment of the invention, FIG. 2 a schematical drawing of an energy image in an energy dataset, FIG. 3 an example view of a result image in a result dataset, FIG. 4 a computed tomography device according to an embodiment of the invention, and FIG. 5 the functional structure of a control device of the computed tomography device of FIG. 4.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CDROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a computer-implemented method for automatically estimating and/or correcting an error due to image artifacts in a multi-energy computed tomography result dataset relating to at least one target material, wherein at least two three-dimensional energy datasets of an imaging region of a patient are acquired using an x-ray imaging device, in particular a computed tomography device, using different x-ray energy spectra and the result dataset is determined by evaluating the energy datasets using material-specific energy dependences of x-ray attenuation, according to the invention, the following steps are performed for estimation of the error due to artifacts:

determining at least one first subregion of the imaging region, which is free from the target material and contains at least one, in particular exactly one, second material with known material-specific energy dependence of x-ray attenuation,
   for each first subregion, comparing the image values of the energy dataset for each voxel, taking into account the known energy dependence, to determine deviation values indicative of artifacts,
   for at least a part of the at least one remaining second subregion of the imaging region, calculating estimated deviation values by interpolating and/or extrapolating from the determined deviation values in the at least one first subregion, wherein the estimated deviation values are used as estimated error due to artifacts.

It has been discovered in the course of at least one embodiment of the current invention, that most artifacts occurring in multi-energy computed tomography have a low spatial frequency. If such basic artifacts of the energy datasets differ, derived artifacts ("difference artifacts" relating to at least two energy datasets) when evaluating the differences between energy values of different energy datasets result, which also have a low spatial frequency and are highly relevant when evaluating x-ray attenuation changes between different energy spectra. It is these derived or difference artifacts that at least one embodiment of the invention is focused on, to derive their artifact strength.

Due to the low spatial frequency, if an estimation of artifact strength for a large enough portion of the imaging region can be determined, it is possible to extrapolate and/or interpolate these artifact strengths, described by deviation values in at least one embodiment of the current invention, such that conclusions regarding the artifact strength in other, second subregions of the imaging region can be drawn. In particular in medical imaging, areas without the target material, for example iodine or bone, are usually contained in the imaging region and may be determined as first subregions.

In particular, at least one embodiment of the invention proposes the detection and quantification of image artifacts, in particular image artifacts of low spatial frequency, which are relevant for multi-energy evaluation, by analyzing first subregions of the imaging region that do not contain the target material and/or other materials with a strong energy dependency. Suitable second materials in the first subregions may, for example, comprise air surrounding a patient and inside hollow organs of the patient, but also other anatomical subregions, for example containing subcutaneous fat and/or muscle as second materials, can be used.

In a concrete example of an embodiment, without any artifacts present, the energy values (that is, image values of the energy dataset), in particular HU values, of air should be identical for all energy datasets at different energy spectra/energy levels. Differences in energy values indicate the presence of image artifacts, due to basic artifacts differently influencing the energy datasets. The higher the difference, the stronger the multi-energy evaluation relevant artifact might be. By assessing any deviation found and the error propagation within the evaluation process, in particular the material decomposition process, the error of result datasets due to such variations of basic artifacts can be estimated and provided as an additional information alongside the result values, that is, image values of the result dataset, to increase the confidence of the result values. Additionally and/or alternatively, derived information about the strength of the artifacts can be used to apply a respective correction, for example by using a correction algorithm, to the energy datasets, such that also the result datasets are corrected and errors due to image artifacts are at least reduced.

That is, in example embodiments of the current invention, at least one of the energy values, that is, the image values of the energy datasets, is corrected according to the estimated deviation values before determining the result values of the result dataset and/or, additional to the result dataset, an error dataset showing the spatially resolved deviation values and/or the error propagated through the evaluation process is determined, and/or the result dataset is modified, in particular colored, according to the deviation values and/or error values. For example, the deviation values may be provided as additional information by adding a respective colorization to the result dataset, for example indicating regions with higher artifact strength in red and regions having low artifact strength in green, wherein different colors and shades may be used therebetween to provide a high resolution of the additional information.

However, error information may also be provided as an additional dataset, in particular an error dataset showing the spatially resolved deviation values and/or the propagated error values. It is, of course, also possible to propagate the deviation values through the evaluation process, such that error propagation effects are also covered by the resulting error values, which may also be provided as an error dataset. Preferably, however, the deviation values, in particular in the subregions containing the target material, are used for correction of the energy datasets and thus the result dataset.

In embodiments, the at least one first subregion is determined by segmenting the energy datasets regarding at least the at least one second material, wherein, in particular, threshold segmenting and/or an anatomical atlas is used. Such techniques have already been used in the state of the art for other applications and thus need not be described in detail here.

As already explained, preferably, at least one subregion containing a second material having an at least essentially energy-spectra invariant behaviour is used as the at least one first subregion. In particular, the expected change in energy value between the used energy spectra for the second material may be lower than a threshold value. This threshold value may, for example, be chosen as one fifth of a predetermined expected artifact-induced change. For example, in spiral CT, artifacts have been observed that have a strength of, for example, 50 to 80 HU, such that, for example, 65 HU could be chosen as a basis of assessment. On the other hand, for usually employed x-ray energy spectra, for example 80 and 140 kV, the HU value only changes by about 10, which would be well below 20% of 65. In other words, preferably, second materials may be chosen which either do not show measurable change in HU value or whose change in HU value is negligible compared to the expected strength of image artifacts.

It is, however, noted, that it is also possible to choose second materials having a larger dependence on energy spectra variation. As long as this dependence is known, for example, at least one reference energy value may be calculated using the known dependence from the measured energy values in one of the energy datasets. The other measured energy values from other energy datasets may be compared to the respective energy value to determine the deviation value.

However, it is preferred to use a second material whose energy value does not or only negligibly change over the energy spectra, for example air, since energy values of a pair of two energy datasets can directly be compared to determine the deviation value. For example, for air, the expected HU value is −1000 HU for each energy spectrum.

Thus, in concrete, preferred embodiments, air may be used as the second material, while, additionally, fat tissue and/or muscle tissue may be used. In the case of air as second material, the at least one subregion may comprise a region outside the patient and/or at least one hollow organ comprising air, in particular the trachea and/or the intestines and/or at least one lung. Considering the fact that air is also present inside the patient, at least for some imaging regions, along with the air subregions outside the patient, first subregions inside the patient may be chosen additionally, providing further sampling points for deviation values and, consequently, the quality of extrapolation and/or interpolation is improved.

Regarding extrapolation and/or interpolation, newest-neighbor interpolation and/or inverse distance weighting and/or spline interpolation may be employed. Since the artifacts mainly discussed here occur with a low spatial frequency, the strength also varies slowly, such that already simple interpolation and/or extrapolation techniques provide good results regarding the deviation values.

In a concrete example embodiment, the energy datasets may be acquired by spiral computed tomography, wherein, during acquisition, the acquisition arrangement comprising the x-ray source and the x-ray detector also moves in a z-direction (along the rotational axis/along the longitudinal direction of the patient) relatively to the patient/imaging region. Thus, artifactual representation of structures that are changing in shape or position along the z-axis can occur, as they will be in different positions for different projection images used in the reconstruction of the energy dataset. In particular increasing pitch can worsen these artifacts. Such spiral artifacts usually have a low spatial frequency and can thus be adequately described by interpolation and/or extrapolation from certain sampled points.

Other examples for artifacts that may be detected and estimated and/or corrected using the method according to the invention may, for example, include scattering artifacts and/or undersampling artifacts.

It is noted that at least one embodiment of the current invention provides a very simple to realize estimation process yielding good results. From easily discernible first subregions, for example subregions containing air, where deviation values may be easily determined by simple comparison of energy values, that is, image values of the energy datasets, simple extrapolation and/or interposition approaches allow the determination of deviation values for at least one second subregion, in particular containing the target material. These deviation values directly correlate with the strength of artifacts at the corresponding position. However, in some embodiments, the inventive approach may also form the basis for more sophisticated processes.

For example, in embodiments, the interpolation and/or extrapolation may be performed taking into account at least one expected property of at least one of the at least one artifact, in particular an expected spatial frequency or an expected spatial frequency range of the artifacts. In some cases, for example in the case of spiral artifacts, certain acquisition parameters of the x-ray imaging device directly correlate with the expected spatial frequencies of the image artifacts. For example, in spiral CT, when a pitch of about 3 is used, minima and maxima of the spiral artifacts usually follow each other every 6 cm. However, using such information as a constraint during interpolation and/or extrapolation, other artifacts may be suppressed and/or not taken into account, such that such use of prior knowledge should, preferably, be extensive enough to cover all forms of expected artifacts.

In some cases, interpolation and/or extrapolation may include using an artificial intelligence algorithm. Such artificial intelligence algorithms, which may also be called trained functions, may be trained using ground truth information about artifacts in training datasets, for example by employing deep learning approaches. The artificial intelligence algorithm may, for example, comprise a neural network. However, ground truth information about artifacts is hard to determine, in particular for image artifacts of low spatial frequency. In particular, a patient would have to be imaged at least twice, increasing the amount of radiation the patient is subjected to, which would be undesirable. Additionally, using artificial intelligence would require more computation power, while the simpler approaches explained above already yield great results.

It should be noted at this point that, in the case of dual energy computed tomography, only two energy datasets and thus one deviation value can be calculated. However, in the case of more than two energy datasets, deviation values may be determined for each pair of energy datasets, wherein, in an embodiment, one reference energy dataset may be determined and deviation values of all other energy datasets with regard to the reference energy dataset may be determined and used for respective relative correction. However, in other approaches, deviation values may be calculated for each pair and propagated to calculate error values regarding the result dataset by error propagation. Further, statistical methods may be employed to calculate an overall error value and/or determine an overall correction.

At least one embodiment of the inventive method may, for example, be employed regarding iodine measurements. That is, iodine may be used as the target material, wherein, for example, an iodine material map may be determined as at least one of the at least one result dataset. The iodine material map may be quantitative or qualitative.

At least one embodiment of the invention further concerns an x-ray imaging device, in particular a computed tomography device, comprising at least one acquisition arrangement, which comprises an x-ray source and an x-ray detector, and a control device configured to perform a method according to at least one embodiment of the invention. All features and remarks regarding the inventive method analogously apply to the x-ray imaging device according to at least one embodiment of the invention, such that the same advantages are achieved. In this manner, additional information and/or correction may be provided directly at the x-ray imaging device.

A computer program according to at least one embodiment of the invention can be, for example, loaded directly into a storage device of a control device of an x-ray imaging device and comprises program code/segments to perform the steps of a method according to at least one embodiment of the invention when the computer program is executed in the control device of the x-ray imaging device.

The computer program according to at least one embodiment of the invention may be stored on an electronically readable storage medium according to at least one embodiment of the invention, which thus comprises electronically readable control information stored thereon, wherein the control information comprises at least one computer program according to at least one embodiment of the invention and is configured such that a method according to at least one embodiment of the invention is performed if the electronically readable storage medium is used in a control device of an x-ray imaging device.

In summary, at least one embodiment of the current invention allows to access the level of image artifacts in spectral images by comparing in particular energy-spectra invariant first subregions, for example of air or fat, in the energy datasets. In particular when quantitative evaluation is performed, the user receives information about the expected error due to these artifacts in addition to the result values. This allows for an improved diagnosis, since the accuracy of the result values is known to the user, in particular a physician. Quantitative information about the image artifacts levels in the different subregions allows for a respective correction of these image artifacts in the energy datasets and/or directly in the result dataset.

At least one embodiment of the invention, by calculating deviation values, focuses on information relevant to the multi energy CT evaluation process, i.e. "difference artifacts" that are relevant for evaluating the change from one energy spectrum to the other. Such artifacts are the result by having different strengths of basic artifacts in at least two of the at least two energy datasets. Artifact strengths described by deviation values are thus understood to relate to differences between energy datasets, which is exactly the information used in multi energy CT evaluation, for example material decomposition.

FIG. 1 is a flowchart of an embodiment of a method according to the invention. In this embodiment, dual-energy computed tomography of a patient is to be performed to determine a quantitative distribution of iodine, for example for tumor or lesion characterization. In particular, iodine is the target material of the examination.

In a step S1, two energy datasets are acquired at different x-ray energy spectra. For example, one of the spectra may be centered around 80 kV (low energy), the other at 140 kV (high energy). For the acquisition of the three-dimensional energy datasets, a computed tomography device is used such that a spiral trajectory of the x-ray source is achieved. In other words, spiral CT is employed, wherein a patient table carrying the patient is moved through the gantry during rotation of the acquisition assembly. Spiral CT, however, can lead to certain image artifacts, for example spiral artifacts. These artifacts may differ between energy datasets, leading to a distortion of the effects induced by different x-ray attenuation for different energies.

The method described here allows to estimate the strength of such spiral artifacts relevant to dual energy CT evaluation and other artifacts of a low spatial frequency, for example scattering artifacts, that result in different effects in different energy datasets.

In step S1, as known, projection images of an imaging region of the patient are acquired and a three-dimensional energy dataset is reconstructed for each energy spectrum.

In a step S2, at least one first subregion of the imaging region is determined, which is free from the target material, in this case iodine, and contains exactly one second material, in this case air, which has a known material-specific energy dependence of x-ray attenuation, in this case being invariant, meaning the HU value of air should be the same for each energy dataset. The first subregions may be determined using a segmentation algorithm, for example threshold-based segmentation, in particular in combination with information from an anatomic atlas. Of course, other approaches as known in the art may also be employed.

Figure 2:
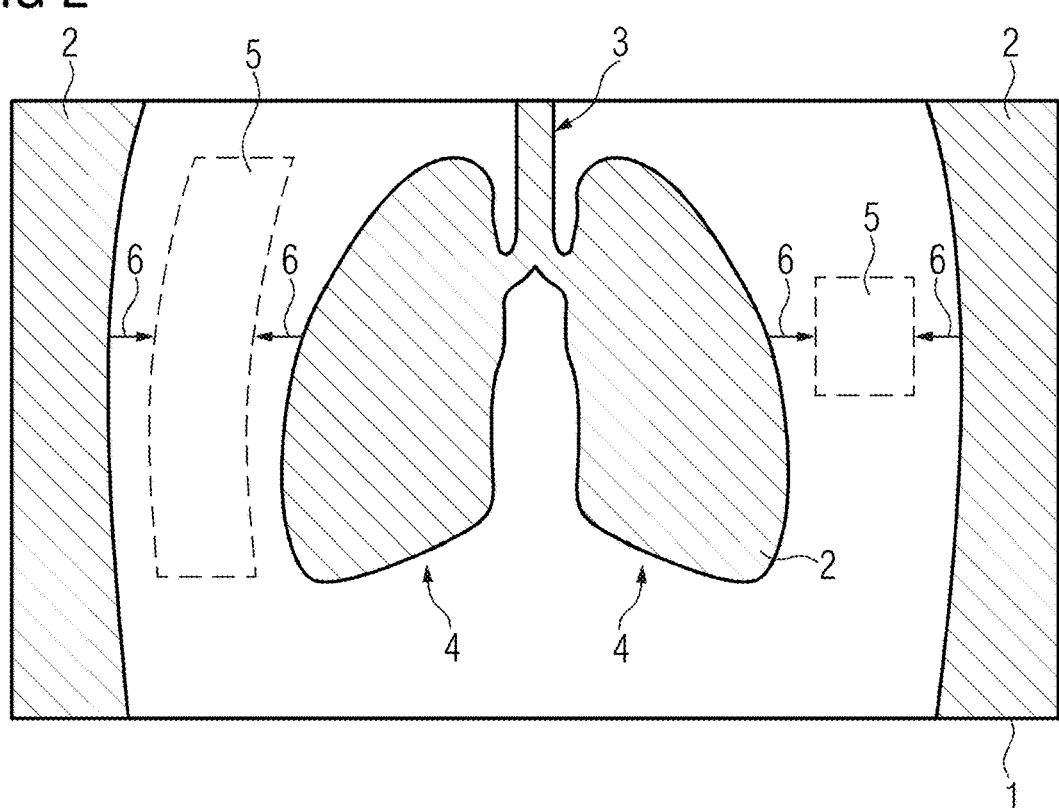

An example two-dimensional energy image of one of the energy datasets, for example an MPR image, is schematically shown in FIG. 2. The energy image 1, in this case, shows parts of three first subregions 2 containing air, namely areas outside the patient (the left and right first subregions 2) and an area comprising the trachea 3 and the lungs 4.

For these first subregions containing air as a second material, since the attenuation behaviour of air is invariant with regard to different energy spectra, for each voxel, the energy values, that is the image value of the energy datasets, for each dataset are compared to determine deviation values. These deviation values indicate the presence of artifacts relevant to the evaluation, since the energy value for air should be the same in each of the energy datasets without artifacts. For example, the deviation values may be determined by computing the difference between the energy value of a voxel of the low energy dataset and the energy value of the voxel in the high energy dataset.

This comparison and determination of the deviation values takes place in step S3 (see FIG. 1). As can be seen from FIG. 2, deviation values over the whole range of the energy datasets are now known, such that a lot of sampling points exist, even inside the patient. This allows, in a step S4, to interpolate and/or extrapolate from the deviation value determined in step S3 to calculate estimated deviation values for second subregions 5 in a step S4. The second subregions 5, as shown in FIG. 2, may be regions of interest (ROI), wherein iodine is expected and the iodine concentration is to be determined. However, it is also possible to cover all remaining parts of the imaging region by at least one second subregion 5.

The process of interpolation and/or extrapolation is indicated in FIG. 2 by arrow 6.

The determined estimated deviation values may be used to correct the energy datasets, however, it is also possible to use them as an error value indicating the strength of image artifacts or using them as a starting point of error propagation, as will be further discussed below.

In a step S5, the energy datasets, possibly corrected, are used, as known in the state of the art, to derive a result dataset, in this embodiment a material map regarding iodine as target material, and/or a quantitative distribution of iodine. Material decomposition approaches may be employed. Parallel to this evaluation, an error propagation process may be performed to propagate the error described by the estimated deviation values in the second subregion 5 through the evaluation process to determine the at least one result dataset.

Figure 3:
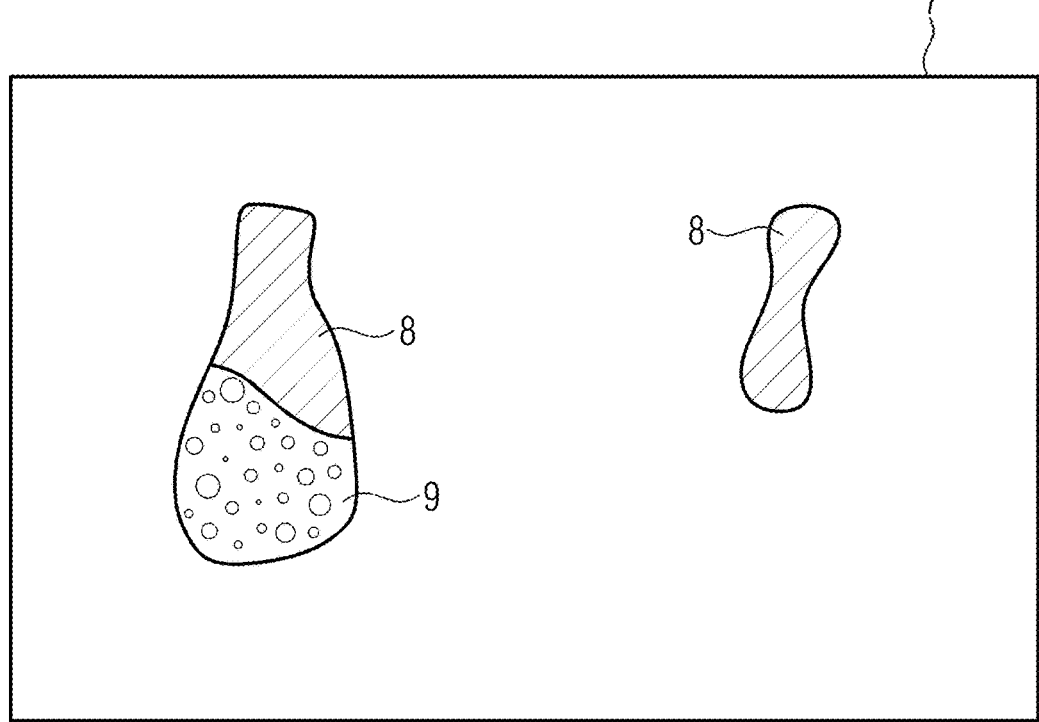

In any case, in a step S6, the voxel-wise error value derived from the error propagation process, in particular provided as an error dataset, or, in other variants, the estimated deviation values as error values, may be used to modify the result dataset for display. For example, as shown in FIG. 3, a result image 7 of the result dataset may use color-coding, as indicated for areas 8, 9 in FIG. 3, inside the second subregions 5 to indicate the reliability of the determined iodine distribution. For example, green color may indicate high reliability, while red may indicate low reliability, that is, large error value.

Of course, other ways to display the estimated error of artifacts may also be used. In variants, it may also be useful, in case the energy datasets have been corrected, to display information regarding the estimated error nonetheless.

Figure 4:
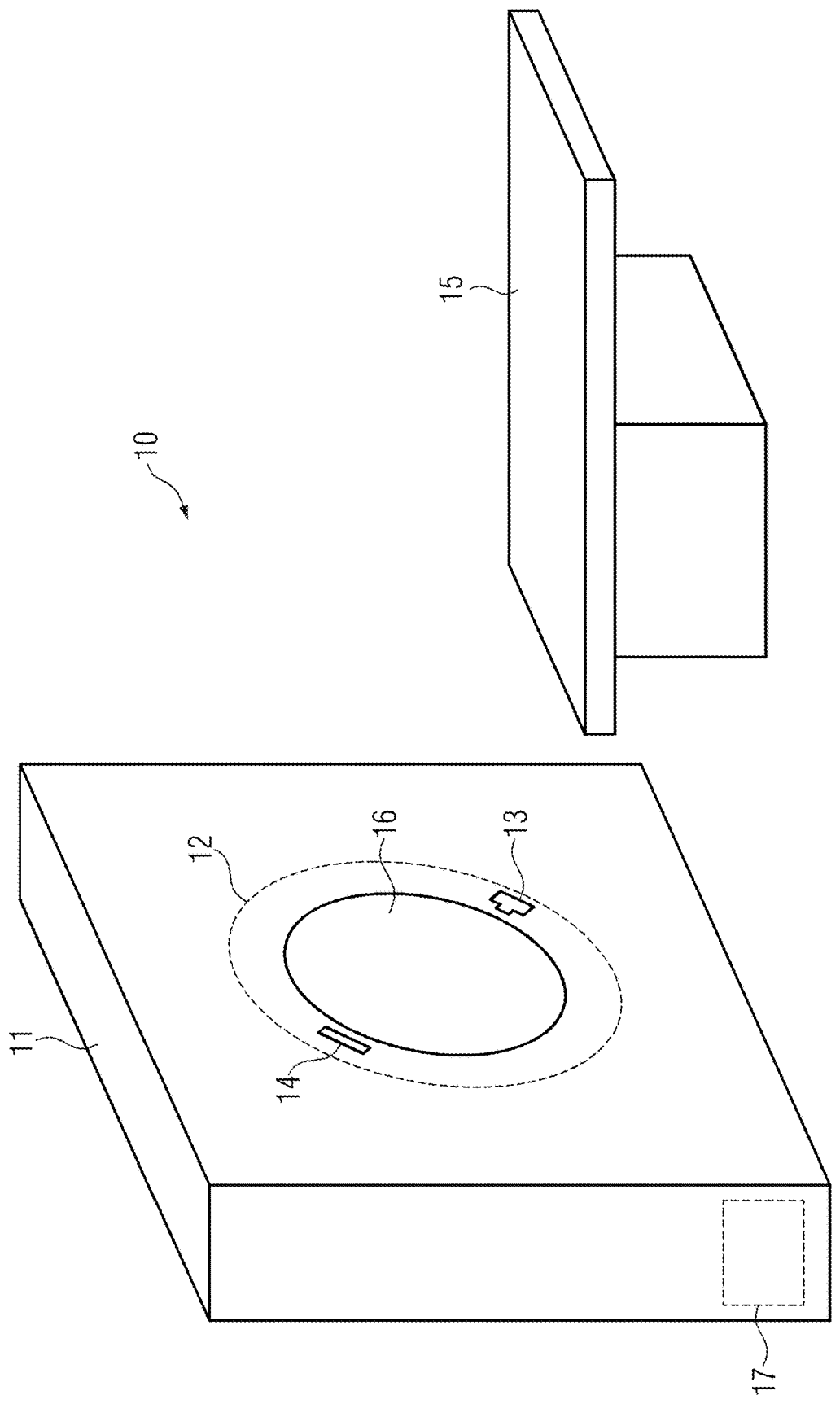

FIG. 4 shows a principle drawing of a computed tomography device 10 according to the current invention. The computed tomography device 10 comprises a gantry 11 in which an acquisition arrangement 12 comprising an x-ray source 13 and an x-ray detector 14 is rotatably mounted. A patient table 15 may be used to position a patient inside an opening 16 of the gantry 11 such that an imaging region may be imaged. Using spiral CT, by in particular continuously moving the table 15 during acquisition of projection images, larger imaging regions may be imaged.

The computed tomography device 10 further comprises a control device 17 for controlling the computed tomography device 10, which is also configured to perform the steps of a method according to an embodiment of the invention.

Figure 5:
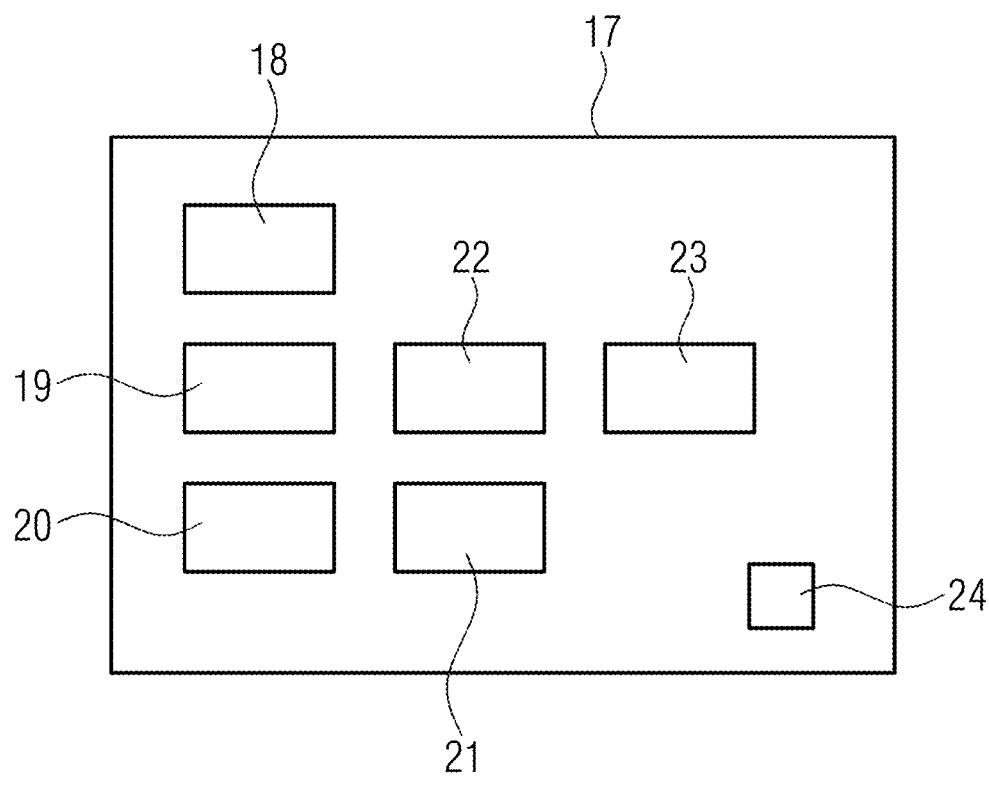

FIG. 5 shows the functional structure of the control device 17. As in principle known from the state of the art, the control device 17 comprises an acquisition device 18 for acquiring image datasets, in particular also energy datasets for multi-energy CT (spectral CT). That is, the acquisition unit 18 is configured to perform S1.

In a determination unit 19, as described with regard to step S2, the first subregion 2 may be determined. A comparison unit 20 compares the energy values of the energy datasets according to step S3, to determine deviation values. These deviation values may be used by a calculating unit 21 to determine estimated deviation values by interpolating and/or extrapolating from the determined deviation values in at least one second subregion 5. The calculation unit 21 may, in some embodiments, also be adapted to correct energy datasets according to the estimated deviation values.

In an evaluation unit 22, the result dataset may be determined as discussed with regard to step S5. In some embodiments, the evaluation unit 22 is further configured to perform the error propagation process to determine an error dataset with propagated error values.

This error dataset or an error dataset comprising the estimated deviation value may be used in a display unit 23 to modify the result dataset for display or to display the error estimation information in the error dataset additionally to the result dataset.

It is noted that the functional units described above may be realized by software and/or hardware in a processor of the control device 17, which also comprises the storage device 24. In particular, the functional units may be implemented in the form of a computer program according to an embodiment of the invention.

Although the present invention has been described in detail with reference to the preferred embodiment, the present invention is not limited by the disclosed examples from which the skilled person is able to derive other variations without departing from the scope of the invention.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for at least one of automatically estimating or automatically correcting an error due to artifacts in a multi-energy computed tomography result dataset relating to at least one target material, at least two three-dimensional energy datasets of an imaging region of a patient being acquired using an x-ray imaging device using different x-ray energy spectra, and a result dataset being determined by evaluating the at least two three-dimensional energy datasets using material-specific energy dependences of x-ray attenuation, the computer-implemented method comprising:

determining at least one first subregion, of the imaging region, free from the at least one target material and containing at least one second material with known material-specific energy dependence of x-ray attenuation;

comparing, for each respective first subregion of the at least one first subregion, image values of each of the at least two three-dimensional energy datasets for each voxel, taking into account known energy dependence, to determine deviation values indicative of artifacts; and calculating, for at least a part of at least one remaining second subregion of the imaging region, estimated deviation values by at least one of interpolating or extrapolating from the deviation values indicative of artifacts in a respective first subregion, wherein the estimated deviation values are used as estimated error due to artifacts.

2. The computer-implemented method of claim 1, wherein at least one of at least one energy value is corrected according to the estimated deviation values before determining result values of the result dataset;

additional to the result dataset, an error dataset showing at last one of spatially resolved estimated deviation values and an error propagated through the evaluating the at least two three-dimensional energy datasets using material-specific energy dependences of x-ray attenuation is determined; or the result dataset is modified according to the estimated deviation values.

3. The computer-implemented method of claim 1, wherein the at least one first subregion is determined by segmenting the at least two three-dimensional energy datasets regarding at least the at least one second material.

4. The computer-implemented method of claim 1, wherein at least one subregion containing a second material having an at least essentially energy-spectra invariant behavior is used as the at least one first subregion.

5. The computer-implemented method of claim 1, wherein at least one of air or fat tissue is used as the second material.

6. The computer-implemented method of claim 5, wherein the at least one first subregion, in a case of air as the second material, includes a region outside at least one of the patient or at least one hollow organ comprising air.

7. The computer-implemented method of claim 1, wherein, for the at least one of interpolating or extrapolating, at least one of nearest-neighbor interpolation, inverse distance weighting or spline interpolation is employed.

8. The computer-implemented method of claim 1, wherein the at least two three-dimensional energy datasets are acquired by spiral computed tomography, and wherein the artifacts comprise spiral artifacts.

9. The computer-implemented method of claim 1, wherein the at least one of interpolating or extrapolating is performed taking into account at least one expected property of at least one of the artifacts.

10. The computer-implemented method of claim 1, wherein at least one of iodine is used as the target material; or at least one material map is determined as the result dataset.

11. An X-ray imaging device, comprising:

at least one acquisition arrangement including an x-ray source and an x-ray detector; and a controller to perform determining at least one first subregion, of an imaging region, free from at least one target material and containing at least one second material with known material-specific energy dependence of x-ray attenuation;

comparing, for each respective first subregion of the at least one first subregion, image values of each of at least two three-dimensional energy datasets for each voxel, taking into account known energy dependence, to determine deviation values indicative of artifacts; and calculating, for at least a part of at least one remaining second subregion of the imaging region, estimated deviation values by at least one of interpolating or extrapolating from the deviation values indicative of artifacts in a respective first subregion, wherein the estimated deviation values are used as estimated error due to artifacts.

12. A non-transitory computer program product storing a computer program which, when the computer program is executed on a control device of an x-ray imaging device, performs the method of claim 1.

13. A non-transitory electronically readable storage medium, storing a computer program which, when the computer program is executed on a control device of an x-ray imaging device, performs the method of claim 1.

14. The computer-implemented method of claim 2, wherein the at least one first subregion is determined by segmenting the energy datasets regarding at least the at least one second material.

15. The computer-implemented method of claim 3, wherein at least one of threshold segmenting or an anatomical atlas is used.

16. The computer-implemented method of claim 4, wherein an expected change in an image value between an energy spectra for the second material is relatively lower than a threshold value.

17. The computer-implemented method of claim 16, wherein the expected change in the image value between energy spectra for the second material is relatively less than one fifth of a threshold expected artifact-induced change.

18. The computer-implemented method of claim 2, wherein, for the at least one of interpolating or extrapolating, at least one of nearest-neighbor interpolation, inverse distance weighting or spline interpolation is employed.

19. The computer-implemented method of claim 2, wherein the energy datasets are acquired by spiral computed tomography, and wherein the artifacts comprise spiral artifacts.

20. The computer-implemented method of claim 9, wherein the at least one expected property of at least one of the artifacts is an expected spatial frequency or an expected spatial frequency range of the artifact.

21. The X-ray imaging device of claim 11, wherein the X-ray imaging device is a computed tomography device.

* * * * *